United States Patent
Perrier et al.

(10) Patent No.: US 9,133,279 B2
(45) Date of Patent: Sep. 15, 2015

(54) CROSS-LINKED POLYMER OF CARBOHYDRATE, NOTABLY BASED ON POLYSACCHARIDES, AND/OR ON OLIGOSACCHARIDES AND/OR ON POLYOLS

(75) Inventors: Eric Perrier, Les Cotes d'Arey (FR); Nabil Abdul-Malak, Caluire (FR); Julie Saget, Lyons (FR)

(73) Assignee: BASF BEAUTY Care Solutions France S.A.S., Lyon (FR)

( * ) Notice: Subject to any disclaimer, the term of this patent is extended or adjusted under 35 U.S.C. 154(b) by 1293 days.

(21) Appl. No.: 11/174,414

(22) Filed: Jul. 1, 2005

(65) Prior Publication Data
US 2006/0188465 A1 Aug. 24, 2006

(30) Foreign Application Priority Data
Feb. 18, 2005 (FR) ..................... 05 01674

(51) Int. Cl.
| | |
|---|---|
| A61K 31/765 | (2006.01) |
| A61K 8/73 | (2006.01) |
| C08G 63/91 | (2006.01) |
| C08B 37/00 | (2006.01) |
| A61Q 19/00 | (2006.01) |
| C07H 3/02 | (2006.01) |
| C07H 3/04 | (2006.01) |
| C07H 3/06 | (2006.01) |
| C08B 11/193 | (2006.01) |
| C08B 11/20 | (2006.01) |
| C08B 15/00 | (2006.01) |
| C08B 15/10 | (2006.01) |
| C08B 30/18 | (2006.01) |
| C08B 31/00 | (2006.01) |
| C08B 33/00 | (2006.01) |
| C08B 35/00 | (2006.01) |
| C08B 37/08 | (2006.01) |
| A61Q 1/06 | (2006.01) |
| A61Q 5/02 | (2006.01) |
| A61Q 19/06 | (2006.01) |
| A61Q 19/10 | (2006.01) |

(52) U.S. Cl.
CPC ............... *C08B 37/0033* (2013.01); *A61K 8/73* (2013.01); *A61Q 19/00* (2013.01); *C07H 3/02* (2013.01); *C07H 3/04* (2013.01); *C07H 3/06* (2013.01); *C08B 11/193* (2013.01); *C08B 11/20* (2013.01); *C08B 15/005* (2013.01); *C08B 15/10* (2013.01); *C08B 30/18* (2013.01); *C08B 31/003* (2013.01); *C08B 31/006* (2013.01); *C08B 33/00* (2013.01); *C08B 35/00* (2013.01); *C08B 37/00* (2013.01); *C08B 37/003* (2013.01); *C08B 37/009* (2013.01); *C08B 37/0024* (2013.01); *C08B 37/0039* (2013.01); *C08B 37/0042* (2013.01); *C08B 37/0072* (2013.01); *C08B 37/0084* (2013.01); *C08B 37/0087* (2013.01); *C08B 37/0093* (2013.01); *C08B 37/0096* (2013.01); *A61Q 1/06* (2013.01); *A61Q 5/02* (2013.01); *A61Q 19/06* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 2,148,951 A | 2/1939 | Maxwell et al. | |
| 4,152,170 A | 5/1979 | Nagase et al. | |
| 4,226,264 A | 10/1980 | Bridgeford | |
| 5,562,924 A | 10/1996 | Perrier et al. | |
| 5,840,338 A | 11/1998 | Roos et al. | |
| 5,912,016 A | 6/1999 | Perrier et al. | |
| 6,197,757 B1 | 3/2001 | Perrier et al. | 514/53 |

FOREIGN PATENT DOCUMENTS

| | | | |
|---|---|---|---|
| DE | 196 43 066 A1 | 4/1998 | ............ A61K 7/48 |
| DE | 199 32 216 A1 | 1/2000 | ............ C08B 37/00 |
| DE | 199 20 557 A1 | 11/2000 | ............ C08B 37/08 |
| ES | 2 155 793 | 5/2001 | ............ B01J 13/16 |
| FR | 2 780 901 | 1/2000 | |
| GB | 2 043 668 A | 10/1980 | ............ C08B 31/10 |
| GB | 2 151 244 A | 7/1985 | ............ C08B 37/00 |
| JP | 2004217590 | 8/2004 | |
| WO | 94/18944 | 9/1994 | |
| WO | 03/040216 A1 | 5/2003 | |
| WO | WO 2004/092222 | 10/2004 | ............ C08B 37/00 |

OTHER PUBLICATIONS

Definition of xanthan gum from thefreedictionary.com, 2010.*
Patent Abstracts of Japan, abstracting JP 2004-217590.
French Search Report for French Application No. 0501674, dated Oct. 19, 2005.

* cited by examiner

*Primary Examiner* — Layla Bland
(74) *Attorney, Agent, or Firm* — Drinker Biddle & Reath LLP

(57) ABSTRACT

The invention discloses a cross-linked polymer of at least one carbohydrate component comprising at least one primary alcohol function in particular for the manufacture of a composition which is intended to be applied onto the skin to obtain a tensing and/or toning effect.

19 Claims, No Drawings

CROSS-LINKED POLYMER OF CARBOHYDRATE, NOTABLY BASED ON POLYSACCHARIDES, AND/OR ON OLIGOSACCHARIDES AND/OR ON POLYOLS

The present invention relates to the preparation of an active principle having a tensing effect, based on various protein or peptide substances, so as to avoid problems of allergies encountered with these substances. The present invention thus relates to the preparation of cross-linked polymers of carbohydrates.

STATE OF THE ART

Cosmetic formulations very often contain substances which enable characteristic tensing effects to be induced. These effects in particular enable improving the perception of effectiveness of a cosmetic formulation by sensory effects which are perceived significantly by consumers.

Furthermore, these tensing effects enable on the one hand an immediate but temporary reduction to be brought about of the wrinkles and small wrinkles of the skin, and, on the other hand, a tension of the skin used for the formulations of eye surround, neck, neckline or hand type.

Bovine serum albumin or collagen have been the molecules which have been the most used in the past from amongst the substances which are the best known for this property. More recently, the substances developed for this activity are turned towards substances of plant origin: plant proteins have in particular be widely used for this activity.

Thus, for example, the plant albumin fraction of cereal grains or of leguminous plants has been the subject of a particularly interesting patent for its analogy with bovine serum albumin (Coletica, FR 2,701,847, WO94/18944). Similarly, the polymerization of plant proteins with the aid of bifunctional agents has been described for various cosmetic applications (Coletica, FR 2,766,090 (corresponding to U.S. Pat. No. 5,912,016); FR 2,780,901, (corresponding to U.S. Pat. No. 6,197,757). The substances prepared by polymerization of hydrolyzed fractions of plant proteins have also been described and used for tensing effects in cosmetics (FR 2,832, 157, WO 03/040216 A1).

However, the use of proteins in cosmetics becomes problematic since they can induce more or less strong immune reactions, even allergies which can lead to total intolerances. The proteins originating from wheat, nuts, hazelnuts, peanuts, milk, are a few examples of them which are well known to the person skilled in the art.

It is necessary to consider that in the future, compounds of a character which is irritant for the skin, such as proteins, will no longer be able to be used, or little usable, in cosmetics, notably due to legislation.

A particular solution is not described in the prior art which would have enabled the inventors to find an obvious solution to alleviate the problems of irritation of the compounds which can be used in cosmetics or in pharmaceuticals for their tensing effect.

AIMS OF THE INVENTION

A main aim of the invention is to solve the novel technical problem consisting of providing a compound which be capable of obtaining a tensing and/or toning effect on the cutaneous surface in a way which is perceptible by the users, without inducing any identifiable allergic reaction.

An aim of the present invention is to solve the technical problem consisting of providing a toning solution which is preferably based on a starting material of excellent biocompatibility, of total biodegradability, of complete assimilation, of total innocuousness, originating from a renewable biological material, and being able to be present not only in the animal kingdom, but also in the plant kingdom, and also being able to be produced by microbial fermentation.

An aim of the present invention is also to solve the technical problem consisting of providing a novel method of manufacture of the compounds which enable solving the technical problem mentioned above.

The whole of these technical problems is solved for the first time in a manner which is satisfactory, inexpensive, which can be used on an industrial scale, notably cosmetic scale.

DESCRIPTION OF THE INVENTION

Starting off from the prior art known to the inventors, i.e. of polymerized proteins, the inventors have discovered in a surprising way that cross-linked polymers of at least one type of carbohydrate or carbohydrate derivative enabled a tensing and/or toning effect to be obtained of a cutaneous tissue, such as the skin of a human being.

Thus, according to a first aspect, the invention relates to a cross-linked polymer of at least one type of carbohydrate comprising at least one primary alcohol function, and in particular relates to a cross-linked polymer which is obtainable according to the method defined below. This polymer excludes polymers of at least one type of carbohydrate comprising at least one primary alcohol function in the form of capsules or spheres; particularly in the form of microcapsules or of microspheres, or in the form of nanocapsules or of nanospheres.

According to a second aspect, the invention relates to a cosmetic, and/or dermo-pharmaceutical, and/or pharmaceutical composition, comprising a cross-linked polymer as defined above.

Also, according to a third aspect, the invention relates to the use of a cross-linked polymer as defined above, for the manufacture of a composition which is intended to be applied onto a cutaneous tissue of a subject to obtain a tensing and/or toning effect on this tissue.

By the term <<carbohydrate>>, the inventors mean carbohydrates as well as carbohydrate derivatives which comprise at least one, or more, primary alcohol functions.

Within the context of the present invention, the tensing and/or toning effect is mainly measured by virtue of the opinion of volunteers, and/or from measurements of skin roughness, and/or from viscosity of the aqueous solution of the cross-linked carbohydrates, by comparison with the aqueous solution of the non-cross-linked carbohydrates.

According to a variant, the invention relates to the use of the cross-linked polymer, for the manufacture of a composition which is intended to be applied onto a cutaneous tissue of a subject to obtain a reduction of wrinkles and/or small wrinkles of this tissue.

According to another variant, the invention relates to the use of the cross-linked polymer, for the manufacture of a composition which is intended to be applied onto a cutaneous tissue of a subject to improve the biomechanical properties of this tissue.

Advantageously, the composition is a cosmetic, dermo-pharmaceutical or pharmaceutical composition, which is intended to be applied onto at least one part of the face, particularly onto the contour of the eye, and/or of the neck, and/or of the hands, and/or of the neckline, and/or the bust.

The products originating from this invention possess a toning effect upon applying a composition containing them onto the skin. The products originating from this invention do not have any identifiable allergy forming effect upon applying such a composition on the skin.

The products of the invention adsorbent onto the surface of the skin and form an elastic film which is smooth and continuous. The filmogenic, tensing and plastifying properties of the carbohydrates, notably of the polysaccharides, and/or of the oligosaccharides, and/or of the polyols, thus polymerized, are thus particularly interesting.

Advantageously, the products of the invention thus possess filmogenic and/or plastifying properties.

Preferably, the carbohydrate is selected from a polysaccharide, an oligosaccharide, a polyol, and any one of their mixtures.

According to a fourth aspect, the invention relates to a method of cosmetic care comprising topically applying a composition as defined above.

The Applicant knows of a method of polymerization of polysaccharides or of oligosaccharides (COLETICA FR 2,688,422, U.S. Pat. No. 5,562,924). However, this method is a method of interfacial polymerization in an emulsion for the manufacture of microcapsules and of microspheres. Therefore, this method does not enable obtaining a high molecular weight polymer of carbohydrates, other than in the form of spheres and/or capsules, particularly in the form of microcapsules or of microspheres.

Thus, according to a fifth aspect, the present invention describes a method of manufacturing a cross-linked polymer, said method comprising a cross-linking reaction in homogeneous aqueous phase between the primary alcohol function of the carbohydrate and a reactive function of a cross-linking agent, to obtain a cross-linked polymer of at least one type of carbohydrate.

Preferably, the carbohydrate is selected from a polysaccharide, an oligosaccharide, a polyol, and any one of their mixtures.

In a first embodiment, the carbohydrate, particularly the polyol and/or the oligosaccharide, has a molecular weight of greater than or equal to 150 grams per mole (noted as g/mol or Dalton or Da in the rest of the text), preferably of greater than or equal to 2,000 Da.

Advantageously, in this first embodiment the molar ratio of the carbohydrate, particularly of the polyol and/or of the oligosaccharide, with respect to the cross-linking agent, is greater than 0.1, and preferably greater than or equal to 1.

In a second embodiment, the carbohydrate, particularly the polysaccharide, has a molecular weight of greater than or equal to 50,000 Da, preferably greater than or equal to 100,000 Da, more preferably greater than or equal to 300,000 Da. In this case, a hydrolysis can be carried out before the cross-linking reaction, so that the polymerization reaction can lead to polymers mainly soluble. Methods of hydrolyzing carbohydrates are known to the person skilled in the art.

Advantageously, in this second embodiment the molar ratio of the carbohydrate, particularly of the polysaccharide, with respect to the cross-linking agent, is less than 0.1, and preferably less than 0.01.

Advantageously, the polysaccharide comprises 0.5 to 4 primary alcohol functions per diosidic moiety.

Advantageously, the carbohydrate before reaction is in a mixture with an excipient which is acceptable via the topical route, particularly a cosmetically or dermatologically acceptable excipient.

According to another particular embodiment variant, the concentration of carbohydrate having a primary alcohol function, notably of polysaccharide and/or of oligosaccharide, and/or of polyols, is between 0.001% and 50% by weight of the aqueous phase, and more particularly between 0.1 and 10% by weight.

Advantageously, the cross-linking agent is a polyfunctional cross-linking agent, i.e. comprising at least two reactive functions which can react mainly with the primary alcohol function of the carbohydrate, and is advantageously selected from polycarboxylic acid chlorides, carboxylic acid anhydrides, polyisocyanates, polythioisocyanates, polyaldehydes, and any one of their mixtures.

When the carbohydrate has between high molecular, it is preferable that it undergo a hydrolysis prior to the reaction in homogeneous aqueous phase, before being placed in contact with the cross-linking agent.

Advantageously, the method comprises, after the cross-linking reaction, a removal of the compounds which are insoluble in the aqueous phase, when insoluble compounds are present at the end of the reaction.

In a particular embodiment, the method comprises dissolving the carbohydrate in aqueous phase, and then placing in contact with a phase containing the cross-linking agent, which can be dissolved or not in an alcohol such as ethanol and/or butylene glycol, for a period of time which is sufficient to obtain the cross-linking of said carbohydrate and to thus form a cross-linked polymer of carbohydrate, notably of high molecular weight.

As is illustrated in the paragraphs above, the inventors have obtained polymers of carbohydrate of high molecular weight by polymerization in homogeneous aqueous phase. This method is entirely advantageous from the point of view of industrial production, since it limits the number of reaction steps, the cost of starting materials, and also maintains the safety of the personnel.

It was not imaginable that the polymers obtained would have properties known as "tensing effect" properties.

DETAILED DESCRIPTION OF THE INVENTION

The present invention relates in particular to the use of cross-linked carbohydrates, such as polysaccharides, and/or oligosaccharides, and/or polyols, which are cross-linked, notably via their primary alcohol functions, preferably with the aid of a multifunctional agent known to the person skilled in the art.

The present invention relates to a method of preparing carbohydrates comprising a primary alcohol function, notably such as polysaccharides and/or oligosaccharides and/or polyols, which are polymerized (or cross-linked), of high molecular weight, said method comprising the following consecutive steps consisting in:

1) Dissolving, in aqueous phase, a material which is rich in carbohydrates, notably in polysaccharides, and/or in oligosaccharides, and/or in polyols;
2) Polymerizing the carbohydrates by adding a multifunctional agent (cross-linking agent) selected as described above;
3) Optionally removing the reaction products having become insoluble (non-soluble) in the reaction medium.

The method of the present invention enables preparing carbohydrates, notably polysaccharides, and/or oligosaccharides, and/or polyols, which are polymerized (cross-linked) and which are of interest, notably of interest in cosmetics. The polymerized carbohydrates thus obtained have a high molecular weight and surprisingly provide a perfect skin tolerance.

One of the advantages of the method of the present invention is to enable, from a material which is rich in carbohydrates, in polysaccharides and/or in oligosaccharides and/or in polyols, creating a molecular architecture of high molar mass which enables a three-dimensional network to be created which is capable of inducing an improvement of the biomechanical properties of the skin.

It is not easy to provide in a clear manner to define the cross-linked polymer according to the present invention, since the degrees of cross-linking are not identifiable. As an illustration, by the term <<polymer of high molecular weight>>, the inventors mean a polymer which has a significant percentage of chains the molecular weight of which is greater than or equal to 50,000 Daltons, and, particularly for the cross-linked polysaccharides, preferably greater than or equal to 150,000 Daltons, more preferably greater than or equal to 300,000 Daltons.

Other additional or alternative features of the method of the present invention are the following:

The material which is rich in carbohydrates, notably in polysaccharides and/or in oligosaccharides and/or in polyols, is preferably selected from natural substances of plant origin, and/or animal origin, and/or biotechnological origin (e.g. fermentation).

Dissolving in aqueous phase of said material at the rate of 20 g/l to 500 g/l.

According to a particular embodiment, the polysaccharides and/or the oligosaccharides and/or the polyols having primary functions mentioned above are selected from the group consisting of:

The following polysaccharides:
   Galactomannans, for example galactomannans originating from guar such as Viscogum® (SANOFI), or from carob such as those available commercially under the name of Lygomme® (SANOFI) or Meypro-Fleur®, or Meyprodyn® (MEYHALL);
   Carrageenans, such as those extracted from red alga such as those available commercially under the name of Satiagel® or Satiagum® (DEGUSSA) or Genuvisco® (HERCULES);
   Glucomannans, such as those originating from konjac gum, such as those available commercially under the name of Nutricol® (FMC Corporation) or of Propol® (FMC SCHIITZU);
   Polysaccharides having a primary alcohol function originating from fermentation, such as Xanthane (KELKO), Gellane® (KELKO), Curdlane® (TAKEDA) or hyaluronic acid;
   Celluloses, such as Natrosol® 250HHX(AQUALON), Klucel EF® (AQUALON), Vivapur® (Instel Chimos).
   Cellulose derivatives, such as hydroxypropyl methyl cellulose (Aqualon), methyl ethyl cellulose (Aqualon), methyl hydroxy methyl cellulose (Aqualon) or Blanose® (Aqualon);
   Polyholosides, such as Dextran®, Dextran T70, T500 or T2000, dextran sulfate (Pharmacia Fine Chemicals);
   Agars, such as Food grade Agar (Sigma), Bacteriological Agar (Setexam), Monogar M540 Agar (Setexam) or Agar QSN5 (Setexam)
   Alginates, such as sodium salts of alginic acid A2158 (Sigma), Satialgine® (Degussa) or sodium alginate FD 125(Danisco);
   Starches, such as amylopectin (Fluka), amylose (Fluka), Nastar® (Cosucra), Waxy Maize starch (Roquette), Waxillis® (Roquette), starch from wheat (Roquette), starch from rice (Roquette), starch from potato (Roquette), or starch from maize (Roquette);
   Chitosan, such as Kitamer® (Unipex);
   Curdlan, such as Pureglucan® (Takeda);
   Gum adragante or gum tragacanth (Emiga);
   Gum arabic or acacia gum (Colin) or Valgum® (Valmar);
   Chia gum (Sigma);
   Gum elemi (Emiga);
   Gellan gum, such as Kelcogel® (SPCI);
   Gum ghatti or Indian Gum (Sigma);
   Gum karaya (Sigma);
   Shellac (Sigma);
   Manilla gum (Sigma);

The following oligosaccharides, monosaccharides or disaccharides: (marketed by the company Sigma, unless specified otherwise) given as examples:
   Cyclodextrins (particularly α, β, or γ cyclodextrins or their derivatives),
   Dextrins (Glucidex 40® or Glucidex 47®, Roquette);
   Raffinose, cellobiose, sucrose, maltose, lactose, trehalose, dihydroxyacetone (DHA), fructose, sorbose, ribose, deoxyribose, xylose, arabinose, glucose, mannose, galactose, erythrose, threose, allose, atrose, gulose, idose, talose, erythrulose, xylulose, psicose, tagatose, sedoheptulose, xylobiose, chitobiose, nigerose, aminaribiose, kojibiose, sophorose, gentianose, gentiobiose, melibiose, melezitose, turanose, stachyose, verbascose;
   Gluconic acid, gluconolactone, glucosamine, galactosamine, galactosamine sulfate, glucosamine sulfate;
   Saponins, such as saponins from the bark of quillaya;
   Guanosine, uridine;
   Streptomycin sulfate;
   Riboflavin; and The following polyols:(marketed by the company Roquette, unless specified otherwise) given as examples;
   glycerol, sorbitol, erythritol (Sigma), maltitol, sorbitol, mannitol, lactitol (Sigma), galactitol (Sigma), ribitol (Sigma), glycerol (Sigma), xylitol, myro-inositol, polyethylene glycol or PEG having a molecular mass, therefore varied polymerisation level, etc. . . .

According to a particular embodiment, the polysaccharides and/or the oligosaccharides and/or the polyols having primary functions mentioned above are preferably selected from the group consisting of a polysaccharide of xanthan, a cellulose, a gum from carob, xylitol, maltose, a carrageenan, raffinose, an acacia gum, a mixture of glycerol (for example 10%, w/w) and of xanthan (for example 2%, w/w), a mixture of mannitol (for example 10%, w/w) and of inulin (for example 5%, w/w), and any one of their mixtures, which are preferably cross-linked with sebacic acid dichloride or by terephthalic acid dichloride.

According to a particular embodiment, the polysaccharides and/or the oligosaccharides and/or the polyols having primary functions mentioned above are preferably selected from the group consisting of a polysaccharide of xanthan which is cross-linked with sebacic acid dichloride, a cellulose which is cross-linked with sebacic acid dichloride, a gum from carob which is cross-linked with sebacic acid dichloride, xylitol which is cross-linked with sebacic acid dichloride, maltose which is cross-linked with sebacic acid dichloride, a carrageenan which is cross-linked with terephthalic acid dichloride, raffinose which is cross-linked with terephthalic acid dichloride, an acacia gum which is cross-linked with terephthalic acid dichloride, a mixture of glycerol (for example 10%, w/w) and of xanthan (for example 2%, w/w) which is cross-linked with terephthalic acid dichloride, a mixture of mannitol (for example 10%, w/w) and of inulin (for example 5%, w/w) which is cross-linked with terephthalic acid dichloride, and any one of their mixtures.

According to an advantageous embodiment, the method of manufacture is characterized in that a carbohydrate, notably a polysaccharide, and/or an oligosaccharide, and/or a polyol, having primary alcohol functions, is dissolved in aqueous phase, and then this aqueous phase containing the carbohydrate is placed in contact with a phase containing a cross-linking agent, which can be dissolved or not in an alcohol, notably such as ethanol and/or butylene glycol, having functions which are capable of preferentially reacting with the primary alcohol functions of the carbohydrate, to carry out a polymerization between the primary alcohol functions of the carbohydrate and the reactive functions of the cross-linking agent, for a period of time which is sufficient to obtain a polymerized carbohydrate of high molecular weight.

According to an embodiment variant of the method according to the invention, the cross-linking agent is selected from the group consisting of a poly(acid chloride), a poly(acid anhydride), a polyisocyanate, a polythioisocyanate, a polyaldehyde, and any one of their mixtures. A cross-linking agent will advantageously be selected the non-reactive part of which is acceptable for the skin, so as to enable, after neutralization of the reaction, to not carry out separation operations.

The poly(acid chloride) is for example selected from an acid trichloride or an acid dichloride to thus form ester bonds.

Advantageously, the proportion by weight of cross-linking agent dissolved in the alcohol varies in general between 5 and 30%, but is preferably situated between 10 and 20%.

According to a preferred feature, the cross-linking agent is selected from phthalic acid trichlorides, phthalic acid dichlorides, sebacic acid dichlorides, azelaic acid dichlorides, succinic acid dichlorides, dichlorides or trichlorides of a tricarboxylic acid, such as citric acid. The poly(acid anhydride) is for example an acid dianhydride, such as, for example, succinic dianhydride or maleic dianhydride.

According to another particularly advantageous embodiment variant of the method according to the invention, the aqueous phase is an aqueous alkaline phase, i.e. the pH of which is alkaline, therefore greater than 7. A preferred pH range is a pH range between about 7.1 and about 10. A more preferred pH is between 8 and 10, and preferably between 8 and 9. A strong base, such as KOH or NaOH, or a weak base such as ammonia solution, borate, phosphate or carbonate, can be used as base for bringing the aqueous phase to a basic pH.

The cross-linked polymers of carbohydrates according to the present invention are prepared in the form of topical compositions, notably cosmetic, dermo-pharmaceutical, or pharmaceutical compositions. From this, for these compositions, the excipient contains for example at least one compound selected from the group consisting of preservatives, emollients, emulsifiers, surfactants, moisturizers, thickeners, conditioners, matifying agents, stabilizers, antioxidants, texture agents, brightening agents, filmogenic agents, solubilizers, pigments, dyes, perfumes and solar filters. These excipients are preferably selected from the group consisting of amino acids and their derivatives, polyglycerols, esters, polymers and derivatives of cellulose, lanolin derivatives, phospholipids, lactoferrins, lactoperoxidases, sucrose-based stabilizers, E vitamins and its derivatives, natural and synthetic waxes, plant oils, triglycerides, insaponifiables, phytosterols, plant esters, silicones and its derivatives, protein hydrolyzates, jojoba oil and its derivatives, lipo/hydrosoluble esters, betaines, aminoxides, plant extracts, esters of sucrose, titanium dioxides, glycines, and parabens, and more preferably from the group consisting of butylene glycol, steareth-2, steareth-21, glycol-15 stearyl ether, cetearyl alcohol, phenoxyethanol, methyl paraben, ethyl paraben, propylparaben, butylparaben, butylene glycol, natural tocopherols, glycerol, sodium dihydroxycetyl, isopropyl hydroxycetyl ether, glycol stearate, triisononaoine, octyl cocoate, polyacrylamide, isoparaffin, laureth-7, a carbomer, propylene glycol, glycerol, bisabolol, dimethicone, sodium hydroxide, PEG 30-dipolyhydroxysterate, capric/caprylic triglycerides, cetearyl octanoate, dibutyl adipate, grape seed oil, jojoba oil, magnesium sulphate, EDTA, cyclomethicone, xanthan gum, citric acid, sodium lauryl sulphate, mineral waxes and oils, isostearyl isostearate, propylene glycol dipelargonate, propylene glycol isostearate, PEG 8 Beeswax, hydrogenated palm tree heart oil glycerides, hydrogenated palm oil glycerides, lanolin oil, sesame oil, cetyl lactate, lanolin alcohol, castor oil, titanium dioxide, lactose, sucrose, low density polyethylene, and an isotonic saline solution.

Advantageously, the compositions mentioned above are formulated in a form selected from the group consisting of a solution, which is aqueous or oily, a cream or an aqueous gel or an oily gel, notably in a pot or in a tube, notably a shower gel, a shampoo; a milk; an emulsion, a microemulsion or a nanoemulsion, which is notably oil-in-water or water-in-oil or multiple or silicone-containing; a lotion, notably in a glass bottle, a plastic bottle, a measure bottle, an aerosol; an ampoule; a liquid soap; a dermatological bar; an ointment; a foam; and an anhydrous product, preferably which is liquid, pasty or solid, e.g. in a form of a stick, notably in a form of lipstick.

Other aims, features and advantages of the invention will appear clearly to the person skilled in the art upon reading the explanatory description which makes reference to the Examples which are given simply as an illustration and which in no way limit the scope of the invention.

The Examples make up an integral part of the present invention, and any feature which appears novel with respect to any prior state of the art from the description taken in its entirety, including the Examples, makes up an integral part of the invention in its function and in its generality.

Thus, every example has a general scope.

Furthermore, in the Examples, all percentages are given by weight, unless indicated otherwise, temperature is expressed in degrees Celsius unless indicated otherwise, and the pressure is atmospheric pressure, unless indicated otherwise.

EXAMPLES

Example 1

Cross-linking a 2% Aqueous Solution of Xanthan, Demonstration of the Tensing Effect on the Human Skin 1—A preparation of polysaccharide of xanthan (5,000,000 Da) is prepared as follows: 2.10 g of xanthan (KELTROL, SPCI) are dissolved in 93.1 g of cold, demineralized water. 4.8 g of NaHCO$_3$ are then added to the preparation under strong agitation. After complete dissolution, the pH stabilizes at a value of between 8 and 8.4.

2—Preparation of the cross-linking agent: 0.75 g of sebacic acid dichloride are dissolved in 4.25 g of butylene glycol.

3—Cross-linking of the aqueous solution of xanthan: the solution prepared in 2/ is added, under agitation, to the solution prepared in 1/. The whole is left under agitation for 60 minutes, so as to cause a polymerization between the activated diacid on the one hand and the alcohol functions of the polysaccharides on the other hand. This reaction is promoted in basic medium. After reaction, the solution of cross-linked xanthan can be used as such but has insoluble substances. The product can be filtered by filtration carried out for example on a device having a cut-off threshold of 0.22 μm to remove the insolubles.

4—Principle of a measurement of tensing effect: in order to characterize the cosmetic effectiveness of the polymerized polysaccharides produced by the present invention on the biomechanical properties of the skin, the tensing effect is measured mainly with the aid of a device sold under the commercial designation <<Video Digitizer®>>(Courage et Khazaka). Such a device enables measuring the parameter of the skin roughness, which is determined by the relief of the image of the skin presented in the form of <<peaks and valleys>>. The more the roughness diminishes, the greater the tensing effect. Two areas of measurement are determined on the forearm (2 cm×2 cm), 50 mg of the solution prepared in 3/ are applied onto the first area. 50 mg of the solution of non-cross-linked polymer are applied onto the second area. After having left to dry for one minute, the parameter of the volume is measured with the aid of the <<Video Digitizer®>>. This measurement is repeated 10 times for a good homogeneity of the measurements. A tensing effect induces a diminishing of the roughness, measured after treatment. The results are given in the following Table;

| Roughness measured by Video Digitizer ® | | |
|---|---|---|
| | Non-polymerized solution. | Polymerized solution. |
| Before application | 64.22 ± 1.56 | 76.80 ± 0.83 |
| 5 minutes after application | 64.20 ± 1.56 | 61.20 ± 1.24 |
| Reduction of roughness, or tensing effect (%) | 0% | 20.3% |

It is demonstrated by this test that the products of the invention enable a significant tensing effect to be obtained on skins of healthy volunteers.

Example 2

Cross-linking a 2% Aqueous Solution of Xanthan

During step 1 of Example 1, 1% of trisodium citrate is added to the 2% xanthan solution. All the other steps are identical.

The tensing effect is close to the effect obtained in Example 1.

Example 3

Cross-linking a 2% Aqueous Solution of Xanthan

During step 1 of Example 1, 0.4% of (tris[hydroxymethyl]aminomethane) is added to the 2% xanthan solution. All the other steps are identical.

The tensing effect is close to the effect obtained in Example 1.

Example 4

Cross-linking a 2% Aqueous Solution of Xanthan

During step 1 of Example 1, 0.5% of disodium phosphate is added to the 2% xanthan solution. All the other steps are identical.

The tensing effect is close to the effect obtained in Example 1.

Example 5

Cross-linking an Aqueous Solution of Cellulose and Sensory Evaluation

1—Preparation of an aqueous solution of cellulose (1,000,000 Da) as follows: 0.56 g of Natrosol® 250HHX are dissolved in 94.64 g of cold, demineralized water. 4.8 g of $NaHCO_3$ are then added to the preparation under strong agitation. After complete dissolution, the pH stabilizes at a value of between 8 and 8.4.

2—Preparation of the cross-linking agent: 1.5 g of sebacic acid dichloride are dissolved in 8.5 g of butylene glycol.

3—Cross-linking of the aqueous solution of cellulose: the solution prepared in 2/ is added, under agitation, to the solution prepared in 1/. The whole is left under agitation for 60 minutes, so as to cause a polymerization between the activated diacid on the one hand and the alcohol functions of the polysaccharides on the other hand. This reaction is promoted in basic medium. After reaction, the solution of cross-linked Natrosol® 250HHX can be used as such.

4—Principle of a measurement of tensing effect: two areas of measurement are determined on the forearm (2cm×2cm), and 50 mg of the solution of cross-linked Natrosol® 250HHX are applied onto the first area. 50 mg of the solution of non-cross-linked Natrosol® 250HHX are applied onto the second area. After having been left to dry for one minute, the toning sensation is noted by sensory evaluation by a panel of volunteers.

| Sensory evaluation on the human skin | |
|---|---|
| Solution of non-cross-linked Natrosol ® 250HHX. | Solution of cross-linked Natrosol ® 250HHX. |
| + | +++ |

+: tensing effect perceived non-significantly;
+++: tensing effect perceived very significantly.

It is demonstrated by this test that the products of the invention enable a significant tensing effect to be obtained on skins of healthy volunteers, that it is possible to detect by sensory evaluation.

Example 6

Cross-linking an Aqueous Solution of Gum from Carob (300,000 Da)

During step 1 of Example 5, a 5% solution of carob, and preferably a 2% solution of carob, is prepared. All the other steps are identical.

The tensing effect is close to the effect obtained in Example 5.

Example 7

Cross-linking an Aqueous Solution of Xylitol (152 Da)

During step 1 of Example 5, a 5% solution of xylitol is prepared. All the other steps are identical.

The tensing effect is close to the effect obtained in Example 5.

Example 8

Cross-linking an Aqueous Solution of Maltose (342 Da)

During step 1 of Example 5, a 20% solution of maltose is prepared. All the other steps are identical.

The tensing effect is close to the effect obtained in Example 5.

Example 9a

Cross-linking an Aqueous Solution of Carrageenans: Modification of the Rheology 1—Preparation of an aqueous solution of carrageenans (500,000 Da) (Genuvisco®, HERCULES) as follows: 0.55 g of Genuvisco® (HERCULES) are placed in 94.65 g of cold, demineralized water. 4.8 g of $NaHCO_3$ are then added to the preparation under strong agitation. After complete dissolution, the pH stabilizes at a value of between 8 and 8.4.

2—Preparation of the cross-linking agent: 0.1 g of terephthalic acid dichloride are dissolved in 0.9 g of ethanol.

3—Cross-linking of the aqueous solution of carrageenans: the solution prepared in 2/ is added, under agitation, to the aqueous solution prepared in 1/. The whole is left under agitation for 60 minutes, so as to cause a polymerization between the activated diacid on the one hand and the alcohol functions of the polysaccharide on the other hand. This reaction is promoted in basic medium. After reaction, the solution of cross-linked carrageenans can be used as such or can be filtered so as to remove the compounds which are insoluble.

The tensing effect is close to the effect obtained in Example 5.

Principle of a measurement of the viscosity: the measurement of the viscosity is carried out on the aqueous solution of cross-linked polysaccharides versus the aqueous solution of non-cross-linked polysaccharides. The viscosimeter used is a rotation apparatus of Brookfield RVTDV-II type which is used a speed 50 and with needle 04.

Furthermore, the polymerization of the carbohydrates induces an increase in their molecular mass, and this induces an increase in the viscosity in a dissolution medium. The survey of the increase of this viscosity enables the intensity of this polymerization to be measured.

| Measurement of the viscosity | |
|---|---|
| Solution of non-cross-linked carrageenans | Solution of cross-linked carrageenans |
| 588 cps | 2632 cps |

Example 9b

Cross-linking an Aqueous Solution of Prior-Hydrolyzed Carrageenans

1—Preparation of a hydrolyzed aqueous solution of carrageenans (Genuvisco®, HERCULES) as follows: 10 g of Genuvisco® (HERCULES) are placed in 90 g of 0.1 M HCl solution (0.1 mole/liter). The hydrolysis is carried out at 60° C. for 5 hours, under moderate agitation, and is then stopped by neutralization with the aid of 1M NaOH up to a pH of between 8 and 9.

2—Preparation of the cross-linking agent: 0.1 g of terephthalic acid dichloride are dissolved in 0.9 g of ethanol.

3—Cross-linking of the aqueous solution of carrageenans: the solution prepared in 2/ is added, under agitation, to the aqueous solution prepared in 1/. The whole is left under agitation for 60 minutes, so as to cause a polymerization between the activated diacid on the one hand and the alcohol functions of the polysaccharide on the other hand. This reaction is promoted in basic medium. After reaction, the solution of cross-linked carrageenans can be diafiltered so as to remove the salts, and then filtered so as to remove the compounds which are insoluble, or can be used as such.

The tensing effect is greater than that observed in the preceding Examples (and particularly the effect obtained for the product of Example 5).

Example 10

Cross-linking an Aqueous Solution of Raffinose Pentahydrate (594 Da)

During step 1 of Example 9, a 10% solution of raffinose is prepared. All the other steps are identical.

The tensing effect is close to the effect obtained in Example 5, but a very clear emollient effect is detected by the panelists.

Example 11

Cross-linking an Aqueous Solution of Acacia Gum

During step 1 of Example 9, a 5% solution of acacia gum (250,000 Da) is prepared. All the other steps are identical.

The tensing effect is greater than the effect obtained in Example 5.

Example 12

Cross-linking an Aqueous Solution of a Polysaccharide/Polyol Mixture

During step 1 of Example 9, a solution of glycerol (92 Da) (10%, w/w) and of xanthan (2%, w/w) is prepared. All the other steps are identical.

The tensing effect is close to the effect obtained in Example 5, but a very clear emollient effect is detected by the panelists.

Example 13

Cross-linking an Aqueous Solution of an Oligosaccharide/Polyol Mixture

During step 1 of Example 9, a solution of mannitol (182 Da) (10%, w/w) and of inulin (ca. 5000 Da) (5%, w/w) is prepared. All the other steps are identical.

The tensing effect is close to the effect obtained in Example 5, but a very clear emollient effect is detected by the panelists.

Example 14

Use of the Products of the Invention in Cosmetic or Pharmaceutical Formulations of Oil-in-water Emulsion Type

| | Formulation 14a: | |
|---|---|---|
| A | Water | Qsp 100 |
| | Butylene Glycol | 2 |
| | Glycerin | 3 |
| | Sodium Dihydroxycetyl Phosphate, Isopropyl Hydroxycetyl ether | 2 |
| B | Glycol Stearate SE | 14 |
| | Triisononaoin | 5 |
| | Octyl Cocoate | 6 |
| C | Butylene Glycol, Methylparaben, Ethylparaben, Propylparaben, pH adjusted to 5.5 | 2 |
| D | Products of the invention | 0.01–10% |

| | Formulation 14b: | |
|---|---|---|
| A | Water | qsp 100 |
| | Butylene Glycol | 2 |
| | Glycerin | 3 |
| | Polyacrylamide, Isoparaffin, Laureth-7 | 2.8 |
| B | Butylene Glycol, Methylparaben, Ethylparaben, Propylparaben; | 2 |
| | Phenoxyethanol, Methylparaben, Propylparaben, Butylparaben, ethylparaben | 2 |
| | Butylene Glycol | 0.5 |
| D | Products of the invention | 0.01–10% |

| | Formulation 14c: | |
|---|---|---|
| A | Carbomer | 0.50 |
| | Propylene Glycol | 3 |
| | Glycerol | 5 |
| | water | qsp 100 |
| B | Octyl Cocoate | 5 |
| | Bisabolol | 0.30 |
| | Dimethicone | 0.30 |
| C | Sodium Hydroxide | 1.60 |
| D | Phenoxyethanol, Methylparaben, Propylparaben, Butylparaben, ethylparaben | 0.50 |
| E | Perfume | 0.30 |
| F | Products of the invention | 0.01–10% |

Example 15 of the Invention

| Use of the products of the invention in a formulation of water-in-oil type. | | |
|---|---|---|
| A | PEG 30 dipolyhydroxystearate | 3 |
| | Capric Triglycerides | 3 |
| | Cetearyl Octanoate | 4 |
| | Dibutyl Adipate | 3 |
| | Grape Seed Oil | 1.5 |
| | Jojoba Oil | 1.5 |
| | Phenoxyethanol, Methylparaben, Propylparaben, Butylparaben, ethylparaben | 0.5 |
| B | Glycerin | 3 |
| | Butylene Glycol | 3 |
| | Magnesium Sulfate | 0.5 |
| | EDTA | 0.05 |
| | Water | qsp 100 |
| C | Cyclomethicone | 1 |
| | Dimethicone | 1 |
| D | Perfume | 0.3 |
| E | Products of the invention | 0.01–10% |

Example 16 of the Invention

| Use of the products of the invention in a formulation of shampoo or shower gel type. | | |
|---|---|---|
| A | Xantham Gum | 0.8 |
| | water | qsp 100 |
| B | Butylene Glycol, Methylparaben, Ethylparaben, Propylparaben | 0.5 |
| | Phenoxyethanol, Methylparaben, Propylparaben, Butylparaben, ethylparaben | 0.5 |
| C | Citric acid | 0.8 |
| D | Sodium Laureth Sulfate | 40.0 |
| E | Product of the invention | 0.01–10% |

Example 17 of the Invention

| Use of the products of the invention in a formulation of lipstick type and other anhydrous products. | | |
|---|---|---|
| A | Mineral Wax | 17.0 |
| | Isostearyl Isostearate | 31.5 |
| | Propylene Glycol Dipelargonate | 2.6 |
| | Propylene Glycol Isostearate | 1.7 |
| | PEG 8 Beeswax | 3.0 |
| | Hydrogenated Palm Kernel Oil Glycerides, Hydrogenated Palm Glycerides | 3.4 |
| | Lanolin Oil | 3.4 |
| | Sesame Oil | 1.7 |
| | Cetyl Lactate | 1.7 |
| | Mineral Oil, Lanolin Alcohol | 3.0 |
| B | Castor Oil | qsp 100 |
| | Titanium Dioxide | 3.9 |
| | CI 15850:1 | 0.616 |
| | CI 45410:1 | 0.256 |
| | CI 19140:1 | 0.048 |
| | CI 77491 | 2.048 |
| C | Products of the invention | 0.01–5% |

Example 18 of the Invention

| | Use of the products of the invention in a formulation of aqueous gels (eye surrounds, slimmers, etc . . . ) | |
|---|---|---|
| A | water | Qsp 100 |
| | Carbomer | 0.5 |
| | Butylene Glycol | 15 |
| | Phenoxyethanol, Methylparaben, Propylparaben, Butylparaben, Ethylparaben | 0.5 |
| B | Products of the invention | 0.01–10% |

Example 19

Evaluation of the Cosmetic Acceptance of a Preparation Containing the Subject of the Invention Toxicology tests were carried out on the compound obtained according to Example 2 incorporated at 10% in a 0.5% xanthan gel, by an ocular evaluation in the rabbit, by the study of the absence of abnormal toxicity by single oral administration in the rat and by the study of the sensitizing power in the guinea pig.

Evaluation of the Primary Irritation of the Skin in the Rabbit:

The preparations described above are applied without dilution at the dose of 0.5 ml on the skin of 3 rabbits according to the method recommended by the OECD Directive in relation to the study of <<the acute irritant/corrosive effect on the skin>>.

The products are classed according to the criteria defined in the Decision of Jan. 2, 1982 published in the Official Journal of the French Republic (the "JORF") of 21 Feb. 1982.

The results of these tests have enabled concluding that the preparation containing the compound obtained according to Example 2 was classed non-irritant for the skin.

Evaluation of the Ocular Irritation in the Rabbit:

The preparations described above were instilled pure and in one batch at the rate of 0.1 ml in the eye of three rabbits according to the method recommended by the directive of the OECD No. 405 of 24 Feb. 1987 relating to the study of the "acute irritant/corrosive effect on the eyes".

The results of this test enable concluding that the preparations can be considered as non-irritant for the eyes, in the sense of Directive 91/326 EEC, used pure or without dilution.

Test on the Absence of Abnormal Toxicity by Single Oral Administration in the Rat:

The preparations described were administered in one batch orally at the dose of 5 g/Kg of body weight, to 5 male rats and 5 female rats of a protocol inspired from the directive of the OECD No. 401 of $24^{th}$ Feb. 1987 and adapted to cosmetic products.

The LD0 and LD50 are found to be greater than 5,000 mg/Kg. The preparations tested are therefore not classed amongst the preparations which are dangerous by ingestion.

Evaluation of the Skin Sensitization Potential in the Guinea Pig:

The preparations described are subjected to the maximization test described by Magnusson and Kligmann, a protocol which is in agreement with the directive line No. 406 of the OECD.

The preparations described in the preceding Examples are classed as non-sensitizing by contact with the skin.

By comparison, a commercial wheat protein, cross-linked according to the method of Example 1, gives, according to this test protocol, an induced sensitization on 40% of the animals tested.

What is claimed is:

1. A method for manufacturing a cross-linked polymer, comprising cross-linking in a homogenous aqueous phase at least one primary alcohol functional group of xanthan with at least one reactive functional group of sebacic acid dichloride to obtain a cross-linked polymer, wherein the molar ratio of xanthan with respect to sebacic acid dichloride in the homogenous aqueous phase is less than 0.1.

2. The method of claim 1, wherein the molar ratio of xanthan with respect to sebacic acid dichloride in the homogenous aqueous phase is less than 0.01.

3. The method of claim 1, further comprising hydrolyzing said xanthan prior to the cross-linking reaction with sebacic acid dichloride.

4. The method of claim 1, further comprising removing compounds which are insoluble in the aqueous phase after the cross-linking reaction.

5. A method for manufacturing a cross-linked polymer, comprising (1) dissolving xanthan in an aqueous phase to form a xanthan solution, and (2) admixing the xanthan solution of (1) with a phase comprising sebacic acid dichloride to form a homogenous aqueous phase for a period of time sufficient to obtain a cross-linked polymer having a molecular weight of at least 50,000 Daltons, wherein the molar ratio of xanthan with respect to sebacic acid dichloride in the homogenous aqueous phase is less than 0.1.

6. A cross-linked polymer, other than a cross-linked polymer obtained by interfacial polymerization in an emulsion for the manufacture of spheres and capsules, prepared by cross-linking the primary alcohol functional groups of xanthan with sebacic acid dichloride in a homogenous aqueous phase, wherein the molar ratio of xanthan with respect to sebacic acid dichloride in the homogenous aqueous phase is less than 0.1.

7. A cross-linked polymer prepared by (1) dissolving xanthan in an aqueous phase to form a xanthan solution, (2) admixing the xanthan solution of (1) with a phase comprising sebacic acid dichloride to form a homogenous aqueous phase for a period of time sufficient to obtain a cross-linked polymer having a molecular weight of at least 50,000 Daltons, wherein the molar ratio of xanthan with respect to sebacic acid dichloride in the homogenous aqueous phase is less than 0.1.

8. A composition selected from the group consisting of a cosmetic composition, a dermo-pharmaceutical composition, and a pharmaceutical composition, wherein said composition comprises an aqueous solution of the cross-linked polymer of claim 6.

9. A method of cosmetic care selected from the group consisting of tensing skin, toning skin, obtaining a reduction of wrinkles, obtaining small wrinkles, and improving the biomechanical properties of the skin, comprising applying onto the skin the cross-linked polymer as defined in claim 6.

10. The method according to claim 9, wherein the cosmetic care is performed on at least one part selected from the group consisting of face, neck, hands and neckline.

11. A method of cosmetic care selected from the group consisting of tensing skin, toning skin, obtaining a reduction of wrinkles, obtaining small wrinkles, and improving the biomechanical properties of the skin, comprising applying onto the skin the cross-linked polymer as defined in claim 7.

12. The method according to claim 11, wherein the cosmetic care is performed on at least one part selected from the group consisting of face, neck, hands and neckline.

13. A method of cosmetic care comprising topically applying a cosmetic composition comprising the cross-linked polymer as defined in claim 6.

14. A method of cosmetic care comprising topically applying a cosmetic composition comprising the cross-linked polymer as defined in claim 7.

15. The cross-linked polymer of claim 6, wherein the molar ratio of xanthan with respect to sebacic acid dichloride in the homogenous aqueous phase is less than 0.01.

16. The cross-linked polymer of claim 7, wherein the molar ratio of xanthan with respect to sebacic acid dichloride in the homogenous aqueous phase is less than 0.01.

17. The method of claim 5, wherein the molar ratio of xanthan with respect to sebacic acid dichloride in the homogenous aqueous phase is less than 0.01.

18. The method of claim 5, further comprising hydrolyzing said xanthan prior to the cross-linking reaction with sebacic acid dichloride.

19. The method of claim 5, further comprising removing compounds which are insoluble in the aqueous phase after the cross-linking reaction.

* * * * *